(12) United States Patent
Porter et al.

(10) Patent No.: US 7,025,726 B2
(45) Date of Patent: Apr. 11, 2006

(54) DETECTION OF ENDOTHELIAL DYSFUNCTION BY ULTRASONIC IMAGING

(75) Inventors: Thomas R. Porter, Omaha, NE (US); Feng Xie, Omaha, NE (US)

(73) Assignee: The Regents of the University of Nebraska, Lincoln, NE (US)

(*) Notice: Subject to any disclaimer, the term of this patent is extended or adjusted under 35 U.S.C. 154(b) by 0 days.

(21) Appl. No.: 10/764,294

(22) Filed: Jan. 22, 2004

(65) Prior Publication Data

US 2005/0165311 A1 Jul. 28, 2005

(51) Int. Cl.
*A61B 8/06* (2006.01)
(52) U.S. Cl. ..................................................... 600/458
(58) Field of Classification Search ................ 600/438, 600/440–441, 443, 447, 458
See application file for complete search history.

(56) References Cited

U.S. PATENT DOCUMENTS

| | | | |
|---|---|---|---|
| 4,572,203 A | 2/1986 | Feinstein | |
| 4,718,433 A | 1/1988 | Feinstein | |
| 4,774,958 A | 10/1988 | Feinstein | |
| 5,560,364 A | 10/1996 | Porter | |
| 5,567,415 A * | 10/1996 | Porter | ..................... 424/9.52 |
| 5,578,291 A | 11/1996 | Porter | |
| 5,701,899 A | 12/1997 | Porter | |
| 5,980,950 A | 11/1999 | Porter | |
| 6,080,386 A | 6/2000 | Porter | |
| 6,171,246 B1 * | 1/2001 | Averkiou et al. | ........... 600/458 |
| 6,245,747 B1 | 6/2001 | Porter et al. | |
| 6,439,236 B1 | 8/2002 | Porter et al. | |
| 6,537,814 B1 | 3/2003 | Porter et al. | |
| 6,626,831 B1 * | 9/2003 | Holley et al. | ............... 600/437 |

FOREIGN PATENT DOCUMENTS

| | | |
|---|---|---|
| EP | 0398935 | 8/1989 |
| EP | 0441468 A2 | 8/1991 |
| EP | 0458079 A2 | 11/1991 |
| EP | 0458745 A1 | 11/1991 |
| WO | WO 80/02365 A1 | 11/1980 |
| WO | WO 93/17718 A1 | 9/1993 |
| WO | WO 96/07434 A1 | 3/1996 |
| WO | WO 96/39197 A1 | 12/1996 |
| WO | WO 97/29783 A1 | 8/1997 |
| WO | WO 99/13918 | 3/1999 |

OTHER PUBLICATIONS

Panza, Julio A. et al. "Abnormal Endothelium-Dependent Vascular Relaxation in Patients with Essential Hypertension," *The New England Journal of Medicine*. Jul. 1990, 323(1): 22-27.
Levine, M.D., Glenn N. et al. "Cholesterol Reduction in Cardiovascular Disease." *The New England Journal of Medicine*. Feb. 1995, 32(8): 512-521.
Widlansky, MD, Michael E. et al. "The Clinical Implications of Endothelial Dysfunction." *Journal of the American College of Cardiology*. Oct. 2003, 42(7): 1149-1160.

(Continued)

*Primary Examiner*—Francis J. Jaworski
(74) *Attorney, Agent, or Firm*—Patterson & Sheridan, L.L.P.

(57) ABSTRACT

A method for non-invasive detection of vascular endothelial dysfunction using ultrasonic imaging is provided.

37 Claims, 8 Drawing Sheets

OTHER PUBLICATIONS

Anderson, MD, Todd J. et al. "Close Relation of Endothelial Function in the Human Coronary and Peripheral Circulations," *J. Am. Coll. Cardiol.* Nov. 1995, 26(5): 1235-1241.

Rim, MD, Se-Joong et al. "Decrease in Coronary Blood Flow Reserve During Hyperlipidemia is Secondary to an Increase in Blood Viscosity." *Circulation.* 2001, 104: 2704-2709.

Bayfield, MD, Matthew S. et al. "Deoxygenated Blood Minimizes Adherence of Sonicated Albumin Microbubbles During Cardioplegic Arrest and After Blood Reperfusion: Experimental and Clinical Observations with Myocardial Contrast Echocarddiography." *The Journal of Thoracic and Cardiovascular Surgery.* Jun. 1997, 113(6): 1100-1108.

Okumura, MD, Ken et al. "Effect of Acetycholine on the Highly Stenotic Coronary Artery: Difference Between the Constrictor Response of the Infarct-Related Coronary Artery and That of the Noninfarct-Related Artery." *J. Am. Coll. Cardiol.* Mar. 1992, 19(4): 752-758.

Vogel, MD, Robert A. et al. "Effect of a Sincle High-Fat Meal of Endothelial Function in Healthy Subjects." *The American Journal of Cardiology.* Feb. 1997, 79: 350-354.

Anderson, Todd J. et al. "Endothelium-Dependent Coronary Vasomotion Relates to the Susceptibility of LDL to Oxidation in Humans." *Circulation.* May 1996, 93(9): 1647-1650.

Ceriello, MD, Antonio et al. "Evidence for an Independent and Cumulative Effect of Postprandial Hypertriglyceridemia and Hyperglycemia on Endothelial Dysfunction and Oxidative Stress Generation—Effects of Short- and Long-term Simvastatin Treatment." *Circulation.* Sep. 2002, 106: 1211-1218.

Vink, H. et al. "Evidence that cell surface charge reduction modifes capillary red cell velocity—flux relationships in hamster cremaster muscle." *Journal of Physiology.* 1995, 489.1: 193-201.

Lupattelli, MD, Graziana et al. "Flow-mediated vasoactivity and circulating adhesion molecules in hypertriglyceridemia: Association with small, dense LDL cholesterol particles." *American Heart Journal.* Sep. 2000, 140(3): 521-526.

Johnstone, MD, Michael T. et al. "Impaired Endothelium-Dependent Vasodilation in Patients with Insulin-Dependent Diabetes Mellitus." *Circulation.* Dec. 1993, 88(6): 2510-2516.

Porter, MD, Thomas R. et al. "Improved Myocardial Contrast with Second Harmonic Transient Ultrasound Response Imaging in Humans Using Intravenous Perfluorocarbon-Exposed Sonicated Dextrose Albumin." *J. Amm. Coll. Cardiol.* May 1996, 27(6): 1497-501.

Jayaweera, Ananda R. et al. "In Vivo Myocardial Kinetics of Air-Filled Albumin Microbubbles During Myocardial Contrast Echocardiography—Comparison with Radiolabeled Red Blood Cells." *Circ. Res.* Jun. 1994, 74(6).

Porter, Thomas R. et al. "Inhibition of Carotid Artery Neointimal Formation with Intravenous Microbubbles." *Ultrasound in Medicine and Biology.* 2001, 27(2): 259-265.

Keller, MD, Mark W. et al. "Intraoperative Assessment of Regional Myocardial Perfusion Using Quantitative Myocardial Contrast Echocardiography: An Experimental Evaluation." *J. Am. Coll. Cardiol.* Nov. 1990, 16(5): 1267-79.

Hackman, MD, Anne et al. "Levels of Soluble Cell Adhesion Molecules in Patients with Dyslipidemia." *Circulation.* Apr. 1996, 93(7): 1334-1338.

Carlos, Timothy M. et al. "Leukocyte-Endothelial Adhesion Molecules." *Blood.* Oct. 1994, 84(7): 2068-2101.

Christiansen, MB, ChB, Jonathan P. et al. "Noninvasive Imaging of Myocardial Reperfusion Injury Using Leukocyte-Targeted Contrast Echocardiography." *Circulation.* Apr. 2002, 105: 1764-1767.

De man, Frits H. et al. "Not Acute but Chronic Hypertriglyceridemia is Associated with Impaired Endothelium-Dependent Vasodilation—Reversal After Lipid-Lowering Therapy by Atorvastatin." *Arterioscler, Thromb. Vasc. Biol.* Mar. 2000, 20: 744-750.

Celermajer, Ph.D., David S. et al. "Passive Smoking and Impaired Endothelium-Dependent Arterial Dilatation in Healthy Young Adults." *N. Engl. J. Med.* Jan. 1996, 34(3): 150-4.

Eskurza, MD, Iratxe et al. "Pharmacologic Versus Flow-Mediated Assessments of Peripheral Vascular Endothelial Vasodilatory Function in Humans." *The American Journal of Cardiology.* Nov. 2001, 88: 1067-1069.

Ruiz-Ortega, M. et al. "Fourth International Seminar on Cardiovascular Biology and Medicine: Part II." *Hypertension.* Dec. 2001, 38: 1382-1387.

Abe, Yasunori et al. "Soluble Cell Adhesion Molecules in Hypertriglyceridemia and Potential Significance on Monocyte Adhesion." *Arterioscler. Thromb. Vasc. Biol.* May 1998, 18: 723-731.

Neunteufl, Thomas et al. "Systemic endothelial dysfunction is related to the extent and severity of coronary artery disease." *Atherosclerosis.* 1997, 129: 111-118.

Anderson, MD, Todd J. et al. "Systemic Nature of Endothelial Dysfunction in Atherosclerosis." *Am. J. Cardiol.* Feb. 1995, 75: 71B-74B.

Corretti, Mary C. et al. "Technical aspects of evaluating brachial artery vasodilation using high-frequency ultrasound." *Am. J. Physiol.* 1995, 268: H1397-H1404.

Lundman, MD, PIA et al. "Transient Tryglyceridemia Decreases Vascular Reactivity in Young, Healthy Men without Risk Factors for Coronary Heart Disease." *Circulation.* Nov. 1997, 96(10): 3266-3268.

Weller, PhD., Gregory E.R. et al. "Ultrasound Imaging of Acute Cardiac Transplant Rejection with Microbubbles Targeted to Intercellular Adhesion Molecule-1." *Circulation.* Jul. 3003, 108: 218-224.

Villanueva, Flordeliza S. et al. "Albumin Microbubble Adherence to Human Coronary Endothelium: Implications for Assessment of Endothelial Function Using Myocardial Contrast Echocardiography." *J. Am. Coll. Cardiol.* 1997, 30: 689-93.

Lindner, M.D., Jonathan R. et al. "Albumin Microbubble Persistence During Myocardial Contrast Echocardiography is Associated with Microvascular Endothelial Glycocalyx Damage." *Circulation.* 1998, 98: 2187-94.

Masugata, M.D., Hisashi et al. "Comparison of Microbubble Agents that Produce Different Myocardial Signal Intensity for Quantification of Myocardial Blood Flow by Myocardial Contrast Echo." *The American Journal of Cardiology.* Sep. 2001, 88: 714-718.

Phillips, P.J. "Contrast Pulse Sequences (CPS): Imaging Nonlinear Microbubbles." *IEEE Ultrasonics Symposium.* 2001, 1739-45.

Venneri, Lucia et al. "Detection of Carotid Artery Endothelial Function with Intravenous Microbubbles." *The Online Abstract.* 2003.

Celermajer, David S. "Endothelial Dysfunction: Does It Matter? Is It Reversible?" *J. Am. Coll. Cardiol.* Aug. 1997, 30(2): 325-33.

Fisher, MBBS, Nicholas G. et al. "Influence of Microbubble Surface Charge on Capillary Transit and Myocardial Contrast Enhancement." *J. Am. Coll. Cardiol.* 2002, 40(4): 811-9.

Kaul, S. "Instrumentation for contrast echocardiography: technology and techiques," *Am. J. Cardiol.* Nov. 2002, 19(90) Suppl 10A:8J-14J. *National Center for Biotechnology Information.* Apr. 14, 2003 <wysiwyg://http://www.ncbi.nlm.nih.go. PubMed&List_uids=12450584&dopt=Abstract>.

Villanueva, F.S. et al. "Microbubble-endothelial cell interactions as a basis for assessing endothelial function." *Echocardiography.* Jul. 2002, 19(5): 427-38. *National Center for Biotechnology Information.* Mar. 28, 2003 <http://www.ncbi.nlm.nih.gov/entrez/query.fcgi?cmd=Retrieve&db=PubMed&list_uids=12 . . . <.

Lindner, M.D., Jonathan R. et al. "Microbubble Persistence in the Microcirculation During Ischemia/Reperfusion and Inflammation is Caused by Integrin- and Complement-Mediated Adherence to Activated Leukocytes." *Circulation.* 2000, 101: 668-75.

Lindner, M.D., Jonathan R. et al. "Noninvasive Ultrasound Imaging of Inflammation Using Microbubbles Targeted to Activated Leukocytes." *Circulation.* 2000, 102: 2745-50.

Kilbanov, A.L. et al. "Targeting and ultrasound imaging of microbubble-based contrast agents." *Magma.* Aug. 1999, 8(3): 177-84. *National Center Biotechnology Information.* Mar. 28, 2003. <http://www.ncbi.nlm.nih.gov/entrez/query.fcgi?cmd=Retrieve&db=PubMed&list_uids=10 . . .>.

Lindner, M.D., Jonathan R. et al. "Ultrasound Assessment of Inflammation and Renal Tissue Injury with Microbubbles Targeted to P-Selectin." *Circulation.* 2001, 104: 2107-2112.

* cited by examiner

DETECTION OF ENDOTHELIAL DYSFUNCTION BY ULTRASONIC IMAGING

FIELD OF INVENTION

The field of invention is medical imaging. More specifically, the field of the invention is imaging dysfunctional endothelial tissue in intact vasculature by ultrasonic methods.

BACKGROUND OF THE INVENTION

Attention recently has focused on the relationship between endothelial dysfunction and coronary artery disease (Widlansky, et al., *J. Am. Coll. Cardiol.*, 42: 1149–60 (2003) and Okumura, et al., *J. Am. Coll. Cardiol.*, 19: 752–8 (1992)). The term "endothelial dysfunction" refers to a broad class of alterations in endothelial phenotype that may lead to the development of atherosclerosis and other vascular abnormalities (Levine, et al., *New Engl. J. Med.*, 332: 512–21 (1995)), loss of endothelium-dependent vasodilation, and increased expression of leukocyte chemotactic factors, adhesion molecules and inflammatory cytokines (Ruiz-Ortega, et al. *Hypertension,* 38: 1382–7 (2001)).

The methods available currently for studying endothelial function are based on indirect evaluation of vasoreactivity to different stimuli. Stimuli that increase the production of endothelium-derived nitric oxide have been proven useful in assessing endothelium-dependent vasodilation in humans, as has the measurement of vascular response to receptor-dependent agonists such as acetylcholine, bradykinin or substance P. However, important limitations associated with the detection of these vascular responses have to be considered, including the requirement for a local delivery of the agonist via an intra-arterial infusion. Such limitations prevent widespread use of such techniques and carry significant risk of complication. Other techniques in use currently for the assessment of endothelial function provide indirect measurement of the vasoreactivity of brachial arteries using plethysmography or vascular ultrasound. Although studies suggest that endothelium-dependent responses detected in the brachial artery correlate with coronary artery function, these techniques do not allow for direct evaluation of a specific vascular region and do not correlate with microvascular function (Eskurza, et al. *Am. J. Cardiol.*, 88: 1067–9 (2001)).

Recent studies support the hypothesis that the interaction between the endothelium and microbubbles used for myocardial contrast echocardiography could form a basis for studying endothelial dysfunction. Normally microbubbles have kinetics similar to erythrocytes and pass unimpeded through the large vessels and coronary microcirculation (Jayaweera, et al. *Circ. Res.*, 74: 1157–65 (1994)). However, in the presence of dysfunctional endothelium, transit of microbubbles is delayed despite normal blood flow (Villanueva, et al. *J. Am. Coll. Cardiol.*, 30: 689–93 (1997)). Although previous studies have demonstrated that endothelial dysfunction results in retention of microbubbles in the microcirculation (Villanueva, et al. *J. Am. Coll. Cardiol.*, 30: 689–93 (1997) and Christiansen, et al. *Circulation,* 105: 1764–7 (2002)), the value of using microbubbles to detect endothelial dysfunction by direct imaging or imaging of large vessels has not been evaluated to date.

Villanueva et al., in *J. Am. Coll. Cardiol.*, 30: 689–93 (1997), evaluated the influence of the characteristics of the endothelial surface on albumin microbubble transit using an in vitro perfusion model of cultured coronary endothelial cells. This in vitro system demonstrated that microbubbles do not adhere to normal cells, but, during inflammatory conditions, there is binding of microbubbles to exposed extracellular matrix. In the same in vitro model, Villanueva, et al. demonstrated imaging of vascular endothelium using ICAM-binding microbubbles (see WO/99/13918). However, a non-invasive direct method to detect endothelial dysfunction of a specific vessel of interest or in large vessels has not been developed.

There is a need in the art for detecting dysfunction of the endothelium at an early time point to allow early therapeutic intervention to prevent vascular disease before significant damage occurs. The present invention satisfies this need in the art.

SUMMARY OF THE INVENTION

The present invention provides methods that allow for real time detection of endothelial dysfunction, particularly arterial endothelial dysfunction, in major blood vessels by imaging microbubbles retained on vessel endothelium after microbubble injection. Since ultrasound typically destroys microbubbles, a low mechanical index pulse sequence scheme in a high frequency linear array transducer is used to detect retained microbubbles.

Embodiments of the present invention provide one or more of the following advantages over the prior art: detection is performed in real time and is non-invasive; retained microbubbles of specific vessels of interest are visualized directly; microbubbles in large vessels may be visualized; and specialized ligands are not needed for microbubble adherence to the dysfunctional endothelium.

The present invention allows for non-invasive detection of arterial endothelium dysfunction and/or arterial plaque in a patient at an early time point. Endothelium dysfunction has been linked to vascular disease and plaque has been linked to increased incidence of heart attack. Once detected, early therapeutic intervention can be prescribed for the patient.

Thus, in one embodiment of the present invention, there is provided a method for imaging vascular endothelium in a vessel of interest comprising introducing microbubbles into the vasculature of an individual and performing transcutaneous imaging of the vessel of interest using a low mechanical index pulse sequence. The vessel of interest may be any vessel, particularly a large vessel such as a carotid or coronary artery. The low mechanical pulse sequence is performed at a mechanical index of about 0.03 to less than about 0.4, and preferably is performed at a mechanical index of about 0.05 to about 0.3. In addition, the low mechanical index pulse sequence is performed at a frequency of about 1.5 to about 15 MHz, with a frame rate of about 20 to 30 Hz.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

The methods of the present invention allow for real time detection of endothelial dysfunction in major blood vessels by imaging microbubbles retained in vessel endothelium after microbubble injection. Since ultrasound typically destroys microbubbles, a low mechanical index pulse sequence scheme in a high frequency linear array transducer is used to visualize primarily the retained microbubbles. Various embodiments of the present invention provide one or more of the following advantages over the prior art: detection is performed in real time and is non-invasive; microbubbles retained in specific vessels of interest are visualized directly; microbubbles retained in large vessels may be visualized; and specialized ligands are not needed for microbubble adherence to the dysfunctional endothelium. The present invention allows for detection of arterial endothelium dysfunction and/or arterial plaque in a patient at an early time point. Once detected, early therapeutic intervention can be prescribed for the patient.

Before the present methods of vascular endothelial imaging are described, it is to be understood that this invention is not limited to the particular methodology, products, apparatus and factors described, as such methods, apparatus and microbubble formulations may, of course, vary. It is also to be understood that the terminology used herein is for the purpose of describing particular embodiments only, and is not intended to limit the scope of the present invention which will be limited only by appended claims.

Also, it should be noted that as used in this specification and in the appended claims the singular forms "a," "and," and "the" include plural referents unless the context clearly dictates otherwise. Thus, for example, reference to "a factor" refers to one or mixtures of factors, and reference to "the method of production" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated by reference in their entirety for the purpose of describing and disclosing devices, formulations and methodologies which are described in the publication and which might be used in connection with the presently described invention.

In the following description, numerous specific details are set forth to provide a more thorough understanding of the present invention. However, it will be apparent to one of skill in the art that the present invention may be practiced without one or more of these specific details. In other instances, well-known features have not been described in order to avoid obscuring the present invention.

Figure 1:
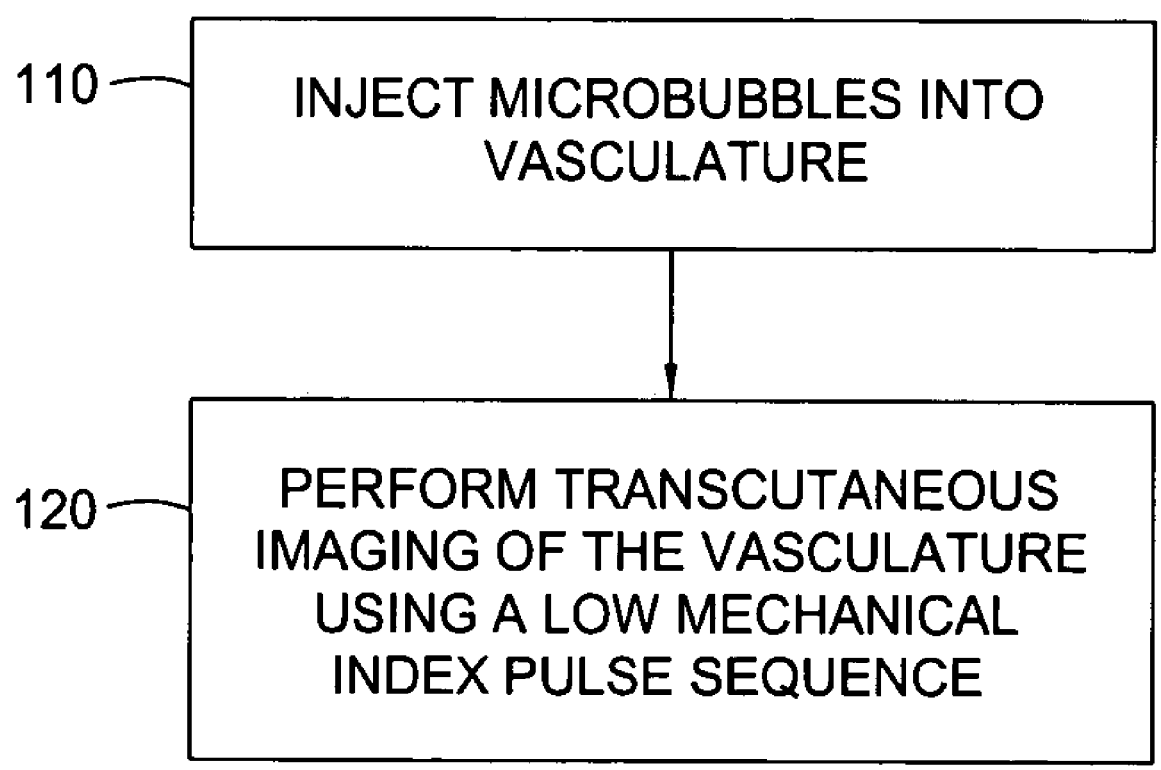
FIG. 1 shows the steps of a simplified method of one embodiment according to the present invention.

FIG. 1 is a simplified flow diagram of the steps of one method according to one embodiment of the present invention. In the first step 110, microbubbles are introduced into the vasculature of an individual, typically either by intravenous or intracoronary injection. Various methods of the present invention employ any appropriate gas-containing ultrasound contrast agent (microbubbles) of any formulation. Representative examples of such contrast agent formulations include microbubbles comprising one or more of the following: proteins, one or more polymer materials, carbohydrates, lipids, phospholipids or surfactants.

Proteins useful in the present invention are those proteins, regardless of source and whether obtained from recombinant biotechnology or by extraction of animal, plant, or microbiological tissue, that are capable of performing the function of stabilizing the microbubbles of the instant invention in an acceptable manner without undue toxicity or physiological or pharmacological effects. Some acceptable biocompatible proteins include but are not limited to albumin, apotransferrin, urease, alpha-1-antitrypsin, alpha fetoprotein, aminotransferases, amylase, C-reactive protein, carcinoembryonic antigen, ceruloplasmin, complement, creatine phosphokinase, ferritin, fibrinogen, fibrin, transpeptidase, gastrin, serum globulins, hemoglobin, myoglobin, immunoglobulins, lactate dehydrogenase, lipase, lipoproteins, acid phosphatase, alkaline phosphatase, alpha-1-serum protein fraction, alpha-2 serum protein fraction, beta protein fraction, gamma protein fraction, gamma-glutamyl transferase, gelatin (e.g. as described in WO-A-8002365), and other proteins.

Synthetic polymers useful in the microbubbles according to certain embodiments of the present invention include synthetic biodegradable polymers such as those described in EP-A-0398935, elastic interfacial synthetic polymers such as those described in EP-A-0458745, microparticulate biodegradable polyaldehydes as described in EP-A-0441468, microparticulate N-dicarboxylic acid derivatives of polyamino acid-polycyclic imides as described in EP-A-0458079, or biodegradable polymers as described in WO-A-9317718 or WO-A-9607434.

Representative examples of carbohydrates include, for example, hexoses such as glucose, fructose or galactose; disaccharides such as sucrose, lactose or maltose; pentoses such as arabinose, xylose or ribose; alpha-, beta- and gamma-cyclodextrins; polysaccharides such as starch, hydroxyethyl starch, amylose, amylopectin, glycogen, inulin, pulullan, dextran, carboxymethyl dextran, dextran phosphate, ketodextran, amincoethyldextran, alginates, chitin, chitosan, hyaluronic acid or heparin; or sugar alcohols, including alditols such as mannitol or sorbitol.

Representative examples of phospholipids useful in the microbubbles of the present invention include lecithins (i.e. phosphatidylcholines), for example natural lecithins such as egg yolk lecithin or soya bean lecithin, semisynthetic (e.g. partially or fully hydrogenated) lecithins and synthetic lecithins such as dimyristoylphosphatidylcholine, dipalmitoylphosphatidylcholine or distearoylphosphatidylcholine; phosphatidic acids; phosphatidylethanolamines; phosphatidylserines; phosphatidylglycerols; phosphatidylinositols; cardiolipins; sphingomyelins; fluorinated analogs of any of the foregoing; mixtures of any of the foregoing and mixtures with other lipids such as cholesterol. The use of phospholipids predominantly (e.g. at least 75%) comprising molecules individually bearing net overall charge, e.g. negative charge, for example as in naturally occurring (e.g. soya bean or egg yolk derived), semisynthetic (e.g. partially or fully hydrogenated) and synthetic phosphatidylserines, phosphatidylglycerols, phosphatidylinositols, phosphatidic acids and/or cardiolipins, for example as described in WO-A-9729783, may be particularly advantageous.

Representative examples of useful surfactants include fatty acids (e.g. straight-chain saturated or unsaturated fatty acids, containing, for example, 10–20 carbon atoms) and carbohydrate and triglyceride esters thereof; phospholipids (e.g. lecithin); fluorine-containing phospholipids; polyethylene glycols; block copolymer surfactants (e.g., polyoxyethylene-polyoxypropylene block copolymers such as Pluronics; extended polymers such as acyloxyacyl polyethylene glycols, for example where the polyethylene glycol moiety has a molecular weight of 2300, 5000 or 10000); and fluorine-containing surfactants (e.g., such as those marketed under the trade names Zonyl and Fluorad, or as described in WO-A-9639197, the contents of which are incorporated herein by reference). Particularly useful surfactants include phospholipids comprising molecules with net overall negative charge, such as naturally occurring (e.g., soya bean- or egg yolk-derived), semisynthetic (e.g., partially- or fully-hydrogenated) and synthetic phosphatidylserines, phosphatidylglycerols, phosphatidylinositols, phosphatidic acids and/or cardiolipins.

Methods of preparing the microbubbles will depend on the microbubble components selected. In one embodiment, the microbubbles useful in the present invention comprise a sonicated solution containing serum albumin, preferably human serum albumin, and a pharmaceutically acceptable saccharide. Exemplary saccharide solutions useful in this invention are aqueous monosaccharide solutions, e.g., those saccharides having the formula $C_6H_{12}O_6$, such as the hexoses (such as glucose), dextrose or fructose; aqueous disaccharide solutions, e.g., those disaccharides having the formula $C_{12}H_{22}O_{11}$, such as sucrose, lactose or maltose; or aqueous polysaccharide solutions, e.g., soluble starches having the formula $(C_6H_{10}O_5)_n$, wherein n is a whole integer between about 20 and about 200, such as amylose or dextran, or mixtures thereof.

In general, a sonicated mixture of commercially available albumin (human) USP solution, and commercially available dextrose, USP for intravenous administration, is employed. Typically, commercially available albumin is supplied as a 5% or 25% by weight sterile aqueous solution, and, USP dextrose is commercially available as a 5% up to about a 70% by weight aqueous solution, with 50% dextrose, injection USP, being preferred. In one embodiment of the present invention, a multifold dilution of aqueous albumin with an aqueous dextrose solution (between about 5% and about 50% by weight) is employed.

Excellent results have been achieved when the contrast agent is sonicated for at least about 80 seconds. The microbubbles useful in the present invention are those that are of sufficiently small size to pass through the microvasculature, yet large enough to permit effective visualization of the vascular endothelium. In general, sonication conditions which produce concentrations of greater than about $4 \times 10^8$/ml of between about 2 and about 10 micron microbubbles are preferred; e.g., see U.S. Pat. Nos. 4,572,203; 4,718,433; 4,774,958; the contents of each of which are incorporated herein by reference. More preferred are microbubbles having a diameter of about 3 to 7 microns, and even more preferred are microbubbles having a diameter of about 4 to 6 microns.

As prepared by the methods described herein, a mean microbubble size ranges from between about 3 to about 7 microns. This has been found to be a good size for use in the present invention as it has been observed that microbubble radius decreases as a function of time in a still liquid due to a diffusion gradient between the internal and external gases of the microbubble. Microbubble size has a significant effect on the persistence of a microbubble within blood, and microbubbles also must be of a size sufficient for transpulmonary passage. Since the size of microbubbles produced by these methods is ideal for transpulmonary passage (between 3 and 7 microns), a reason for an observed loss in videointensity following intravenous injection of microbubbles seen in various applications of vascular imaging is likely due to the diffusion of gases within the microbubble. Because of high surface tension, the concentration of nitrogen and oxygen gas within a microbubble is much higher than that in blood, and thus there is a rapid diffusion of this gas from the interior of the microbubble into the blood stream following intravenous injection. Both nitrogen and oxygen diffuse rapidly across these concentration gradients, but nitrogen appears to dissolve more slowly than oxygen into blood. Since nitrogen is the major component of air, decreasing the concentration gradient for nitrogen across the microbubble improves videointensity following intravenous injection.

It has been found that exposing microbubbles to a nontoxic gas having a lower blood solubility and/or microbubble diffusivity than that of nitrogen and having a gas density of greater than about 0.300 lb/ft$^3$ during sonication increases the size and stability of the microbubbles, while lowering the solubility and diffusivity of the microbubbles in blood. Suitable gases are those which are in gaseous form at 37° C. and that are nontoxic, have a molecular weight of greater than 100 grams/mole, and produce a significantly higher videointensity than, e.g., sonicated albumin alone.

Any appropriate biocompatible gas may be used in the microbubbles of the present invention. The term "gas" as used herein includes any substance (including mixtures) at least partially or completely in gaseous form at the normal human body temperature of 37° C. The gas may comprise air; nitrogen; oxygen; carbon dioxide; hydrogen; an inert gas such as helium, argon, neon, xenon or krypton; a sulphur fluoride such as sulphur hexafluoride, disulphur decafluoride or trifluoromethylsulphur pentafluoride; selenium hexafluoride; an optionally halogenated silane such as methylsilane or dimethylsilane; a low molecular weight hydrocarbon (e.g. containing up to 7 carbon atoms), for example, an alkane such as methane, ethane, a propane, a butane or a pentane; a cycloalkane such as cyclopropane, cyclobutane or cyclopentane; an alkene such as ethylene, propene, propadiene or a butane; an alkyne such as acetylene or propyne; an ether such as dimethyl ether; a ketone; an ester; a halogenated low molecular weight hydrocarbon (e.g. containing up to 7 carbon atoms); or a mixture of any of the foregoing.

Advantageously a halogenated hydrocarbon is employed. In one embodiment, at least some of the halogen atoms in the halogenated gases are fluorine atoms; thus biocompatible halogenated hydrocarbon gases may, for example, be selected from bromochlorodifluoromethane, chlorodifluoromethane, dichlorodifluoromethane, bromotrifluoromethane, chlorotrifluoromethane, chloropentafluoroethane, dichlorotetrafluoroethane, chlorotrifluoroethylene, fluoroethylene, ethylfluoride, 1,1-difluoroethane and perfluorocarbons. Representative perfluorocarbons include perfluoroalkanes such as perfluoromethane, perfluoroethane, perfluoropropanes, perfluorobutanes (e.g. perfluoro-n-butane, optionally in admixture with other isomers such as perfluoro-isobutane), perfluoropentanes, perfluorohexanes or perfluoroheptanes; perfluoroalkenes such as perfluoropropene, perfluorobutenes (e.g. perfluorobut-2-ene), perfluorobutadiene, perfluoropentenes (e.g. perfluoropent-1-ene) or perfluoro-4-methylpent-2-ene; perfluoroalkynes such as perfluorobut-2-yne; and perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane or perfluorocycloheptane. Other halogenated gases include methyl chloride, fluorinated (e.g. perfluorinated) ketones such as perfluoroacetone and fluorinated (e.g. perfluorinated) ethers such as perfluorodiethyl ether. The use of perfluorinated gases, for example sulphur hexafluoride and perfluorocarbons such as perfluoropropane, perfluorobutanes, perfluoropentanes and perfluorohexanes, may be particularly advantageous in view of the recognized high stability in the bloodstream of microbubbles containing such gases. Other gases with physicochemical characteristics which cause them to form highly stable microbubbles in the bloodstream may likewise be useful.

In a preferred embodiment the gas is perfluoropropane, decafluorobutane or perfluorobutane. Generally, the minimum amount of insoluble gas in the microbubbles that is effective is that amount which results in microbubbles which pass reliably through the pulmonary circulation without collapse and is sufficient to lower microbubble gas solubility and diffusivity in vivo in blood.

In one preferred embodiment, the microbubble is a decafluorobutane-enhanced sonicated dextrose albumin solution comprised of a sonicated three-fold dilution of 5% human serum albumin with 5% dextrose. The sonicating system used for sonication may be, for example, a Heat Systems Ultrasonic Processor Model XL2020 (Heat Systems Inc., Farmingdale, N.Y.), with a resonating piezoelectric device. The ½ inch sonicating horn tip is sterilized prior to each sonication. In one exemplary method of sonication, sixteen milliliter aliquots of albumin diluted 1:3 with dextrose are drawn up into a 35 cc "Monoject" syringe (Becton Dickinson and Company, Rutherford, N.J.) and sonicated for 80±0.1 seconds. The "Leur-Lok" of the 35 milliliter syringe is then attached to a stopcock. After mixing the dextrose albumin solution by hand for about 7 to about 10 seconds, the plunger is removed from the top of the syringe. The sterile sonicating horn is then lowered into the open end of the syringe until at the surface of the albumin-dextrose solution. The solution is placed at the horn tip and manually held at this position while continuously sonicating at a frequency of 20,000 Hz and a power output of 210 W for 80±0.1 seconds to form a stable microbubble solution.

During sonication, the dextrose albumin mixture is exposed to perfluoropropane gas (Commercial Grade, 99.9% by weight). The gas is drawn up into a sterile syringe through a 0.22 µM filter (Micron Separations Inc., Westborough, Mass.) to prevent contamination. During sonication, 5 milliliters of perfluoropropane gas is manually injected into the solution, over the 80 second time interval, through the stopcock so that the microbubbles produced contain this less soluble gas. The total volume of perfluoropropane-enhanced sonicated dextrose albumin produced with this formulation is 25±0.2 milliliters. These samples are then used for intravenous injection. Other exemplary methods for microbubble preparation may be found in U.S. Pat. Nos. 5,560,364; 5,567,415; 5,578,291; 5,701,899; 5,980,950; 6,080,386; 6,245,747; 6,439,236; and 6,537,814, the contents of each of which are incorporated herein by reference.

The present invention thus allows in one embodiment, imaging of the endothelium with microbubbles consisting essentially of albumin, a saccharide, and a perfluorocarbon gas. Specialized antibodies or ligands for endothelial cells are not required for microbubble adherence and/or imaging. Therefore, the microbubbles of one aspect of the present invention are easier and less expensive to prepare that those used by, e.g., Villanueva, et al., in WO/99/13918. On the other hand, in other aspects of the present invention the microbubbles may optionally comprise antibodies or ligands specific to endothelium or, more specifically, to dysfunctional endothelium. Such ligands may include but are not limited to ICAM, VCAM, antibodies to metalloproteinases, or agents or ligands that detect elastin-attacking proteins, adhesion molecules or markers for inflammation.

In the next step of FIG. 1, step 120, transcutaneous imaging of the vasculature is performed using a low mechanical index pulse sequence. Generally, ultrasound has been found to be useful for imaging various structures of the body including blood vessels. Ultrasound is a nonionizing form of energy that propagates through a medium as pressure waves. In a basic ultrasound process, a generator produces an electrical pulse and sends it to a transducer. The transducer (or probe) changes the electrical pulse into a sound pulse and sends it into the body. The sound wave travels through a first body tissue until it hits an interface where two different tissues are contiguous. Due to the interface, some of the sound wave will be reflected back and some of the sound wave will continue to travel through the next tissue. The reflected wave is picked up by the transducer and changed into an electrical pulse.

Medical ultrasound applications have been described that use frequencies from as low as 500 KHz to as high as 20 MHz. The methods according to the present invention may be preformed at a wide range of frequencies. The optimal ultrasound frequency for any application represents a tradeoff between the need to acquire ultrasound images with a high degree of spatial resolution, dictating use of higher frequencies, and the need to obtain adequate penetration in the tissue. Imaging depth into tissue is limited by attenuation of the ultrasound waves, and this becomes more severe as the ultrasound frequency is increased. A preferred frequency range for the methods of the present invention is about 1.5 MHz to about 15.0 MHz. A preferred range of frequencies for imaging the carotid artery, for example, is about 3.0 to about 10.0, with a more preferred frequency of about 7.0 MHz. The frame rate for imaging preferably is about 20 to about 30 Hz.

The present invention utilizes a pulse sequence scheme imaging technique allowing for detection of nonlinearly generated signals in the fundamental and harmonic frequency band, which improves sensitivity and specificity of microbubble detection. Since the number of microbubbles that adhere to dysfunctional endothelial cells is small, this higher sensitivity/low mechanical index pulse sequence scheme is ideal for non-invasive characterization of the physiologic features of the endothelium.

Generally, continuous imaging at low transmitted acoustic pressures presents a challenge compared to intermittent imaging with high pressures. Techniques that image with high pressures more easily maintain sensitivity due to strong backscatter. Further, the simple detection of loss-of-correlation signals between two or more pulses offers a means to achieve excellent specificity with high mechanical index imaging. However, as pressure levels are lowered, the loss-of-correlation signals are significantly reduced and specificity is lost. Moreover, at low transmitted pressures the returned signals are generally weak and near the system noise floor. Yet, low transmitted pressures are necessary for continuous imaging in order to minimize microbubble destruction. Thus, physical mechanisms other than loss-of-correlation need to be used to detect microbubbles when operating at low mechanical indexes.

Current single- and multiple-pulse techniques which detect, for example, second harmonic energy due to nonlinear oscillations improve microbubble detectability at low mechanical indexes compared to fundamental imaging and loss-of-correlation-based imaging. However, problems with transducer bandwidths, tissue attenuation, and nonlinear propagation limit performance of such techniques.

On the other hand, the present invention takes advantage of the observation that, the detectability of microbubbles at low mechanical indexes can be improved by processing received nonlinear energy that exists in the same frequency band as the transmitted signal (see, Phillips, *IEEE Trans Ultrason Ferroelectric Frequency Control Symposium*, 1739–45 (2001)). This contrast pulse sequence technique processes nonlinearly-generated signals in the fundamental frequency band to improve sensitivity and specificity to microbubbles compared to second and third harmonic imaging techniques. Indeed, the specificity of sequences sensitive to nonlinear fundamental energy according to the methods of Phillips is significantly greater than the specificity of sequences sensitive to linear fundamental, second harmonic, third harmonic, or LOC signals. The mechanical index found useful in embodiments of the present invention includes a mechanical index of about 0.03 to less than about 0.4, and preferably is about 0.05 to about 0.3.

EXAMPLES

Animal Preparation

The studies performed to demonstrate the effectiveness of the present invention were approved by the Institutional Animal Care and Use Committee of the University of Nebraska Medical Center and conformed to the Position of the American Heart Association on Research Animal Use. Six pigs weighing 35±2 Kg were sedated, endotracheally intubated and placed under general anesthesia using isoflurane. In each animal, 7-Fr catheters were placed on both femoral veins for administration of fluids, microbubbles and intralipid emulsion as well as for withdrawal of blood samples. Both femoral arteries were cannulated for hemodynamic monitoring, and for placing an 8-Fr guide catheter into the proximal left carotid. All pigs were treated with 40 mg of Ketorolac intravenously to prevent pulmonary hypertensive responses to microbubbles (which occur exclusively in this species; see, e.g., Porter, et al. *Ultrasound Med. Bid.*, 27: 259–65 (2001), and ventilated with ambient air during the microbubble injections.

Carotid Artery Response to Acetylcholine

Endothelial function was evaluated by measuring the responses of the carotid artery diameter to incremental doses of the endothelium-dependent vasodilator acetylcholine. Longitudinal sectional images of the carotid artery were obtained with a 7–4 MHz linear transducer (HDI 5000, Philips Medical Systems, Bothell, Wash.). After adequate imaging of the left and right carotid artery with this linear transducer, the skin overlying each vessel was marked to permit monitoring of the vessels at one constant location. Also, a radio opaque marker was positioned at the site to permit identification by angiography.

The diameter of the carotid artery was measured using two-dimensional images of the anterior to posterior inner borders of the vessel at end-diastole, coincident with the R wave on a continuously recorded electrocardiogram (Corretti, et al. *Am. J. Physiol.*, 268: H1397–H1404 (1995)). After acquisition of baseline measurements, the acetylcholine was infused into the carotid artery at incremental concentrations of $10^{-7}$, $10^{-6}$ and $10^{-5}$ Molar, at 10-minute intervals. All settings were optimized at the beginning of the study and maintained throughout the exam. The mechanical index used was 0.8. Measurements of carotid artery diameter were repeated at eight minutes into each infusion. The diameters of three cardiac cycles were obtained for each scan, and the average was utilized for analysis.

Carotid Imaging of Retained Microbubbles

The evaluation of albumin-coated microbubble transit in the carotid artery was performed with a 7.0 MHz linear array transducer equipped with a low mechanical index contrast pulse sequence scheme (Contrast Pulse Sequence, Siemens Acuson Sequoia, Mountain View, Calif.). This transducer transmits pulses of alternating polarity and amplitude in order to detect non-linear responses from microbubbles while simultaneously canceling the linear responses from tissue when at a low mechanical index (Philips, *IEEE Trans Ultrason Ferroelectric Frequency Control Symposium*, 1739–45 (2001)).

Carotid arteries were imaged both in transverse and longitudinal sectional views, in the same position used for the evaluation of diameter responses to acetylcholine. The depth, power output, gain, and compression settings were initially adjusted in order to obtain adequate detection of the microbubbles by real-time imaging and kept constant throughout the exam. The mechanical index used was 0.3 and the frame rate was 24 Hz.

Perfluorocarbon-Exposed Sonicated Dextrose Albumin (PESDA) microbubbles were injected as a bolus of 0.5 ml followed by a 10 ml saline flush into the femoral vein. PESDA was prepared according to the method previously described (Porter, et al. *J. Am. Coll. Cardiol.*, 27: 1497–501 (1996); and U.S. Pat. Nos. 5,560,364; 5,567,415; 5,578,291; 5,701,899; 5,980,950; 6,080,386; 6,245,747; 6,439,236; and 6,537,814). Briefly, a mixture of three parts 5% dextrose and one part of 5% human serum albumin (in a total of 16 ml) was added to 8±2 ml decafluorobutane gas, hand-agited and sonicated with an electromechanical sonicator at 20 kHz for 70–75 seconds. The system used for sonication was a Heat Systems Ultrasonic Processor model XL 2020 (Heat Systems, Inc., Farmingdale, N.Y.). The resulting microbubbles have been shown to have a mean size of 4.6±0.4 microns and a mean concentration (measured by a Coulter counter) of $1.4 \times 10^9$ bubbles/ml.

Transverse sectional images of the carotid artery following each microbubble injection were acquired digitally for quantitative analysis. Retained microbubbles were qualitatively defined as microbubbles adherent to the arterial wall that persisted after clearing the free flowing microbubbles in the lumen of the cariotid artery.

Induction of Endothelial Dysfunction with Intralipid Infusion

Both carotids of each of the four pigs imaged using a real-time pulse sequence scheme and the endothelium-dependent response of the left carotid to intra-arterial infusion of acetylcholine was evaluated. Transient hypertriglyceridemia was then induced by a continuous intravenous infusion of 20% Intralipid (Fresenius Kabi Clayton, L.P., Clayton, N.C.), at a rate of 0.3 ml/Kg/mm, for 10 minutes (see, e.g., Lundman, et al. *Circulation*, 96: 3266–8 (1997) and Rim, et al. *Circulation*, 104: 2704–9 (2001)). Serum triglycerides and cholesterol were measured before and after intralipid infusion. Measurements of carotid responses to acetylcholine infusion and imaging of microbubble retention in the carotid artery were repeated within 30 minutes following intralipid infusion.

Balloon Stretching of Carotid Artery

Both carotid arteries of each of the six pigs were imaged to evaluate the response to physical injury to the endothelium of the artery by a balloon catheter. Baseline carotid angiography was performed by injections of iohexol 300 (Omnipaque, Nycomed, Princeton, N.J.) and the vessel diameter was determined with a manual caliper. After injection of a single bolus of heparin (100 USP U/Kg), an oversized balloon dilation catheter (Guidant; Advanced Cardiovascular Systems, Temecula, Calif.) was advanced under fluoroscopic control into the left common carotid artery of each pig until the radio opaque marker was reached. A 40-millimeter segment of the carotid artery was stretched by inflating the catheter so that it measured 2.2±0.4 mm larger than the angiographic vessel diameter (see, Porter, et al. *Ultrasound Med. Bid.*, 27: 259–65 (2001)). Patency of the carotid artery was confirmed angiographically 10 minutes after the last balloon inflation. After the carotid artery balloon dilatation, intravenous PESDA injections were repeated for imaging of microbubble transit in both the balloon-injured left carotid artery and the control right carotid artery. Following this, carotid artery responses to local acetylcholine infusions were re-evaluated.

Endothelial Acoustic Intensity

Figure 2A:
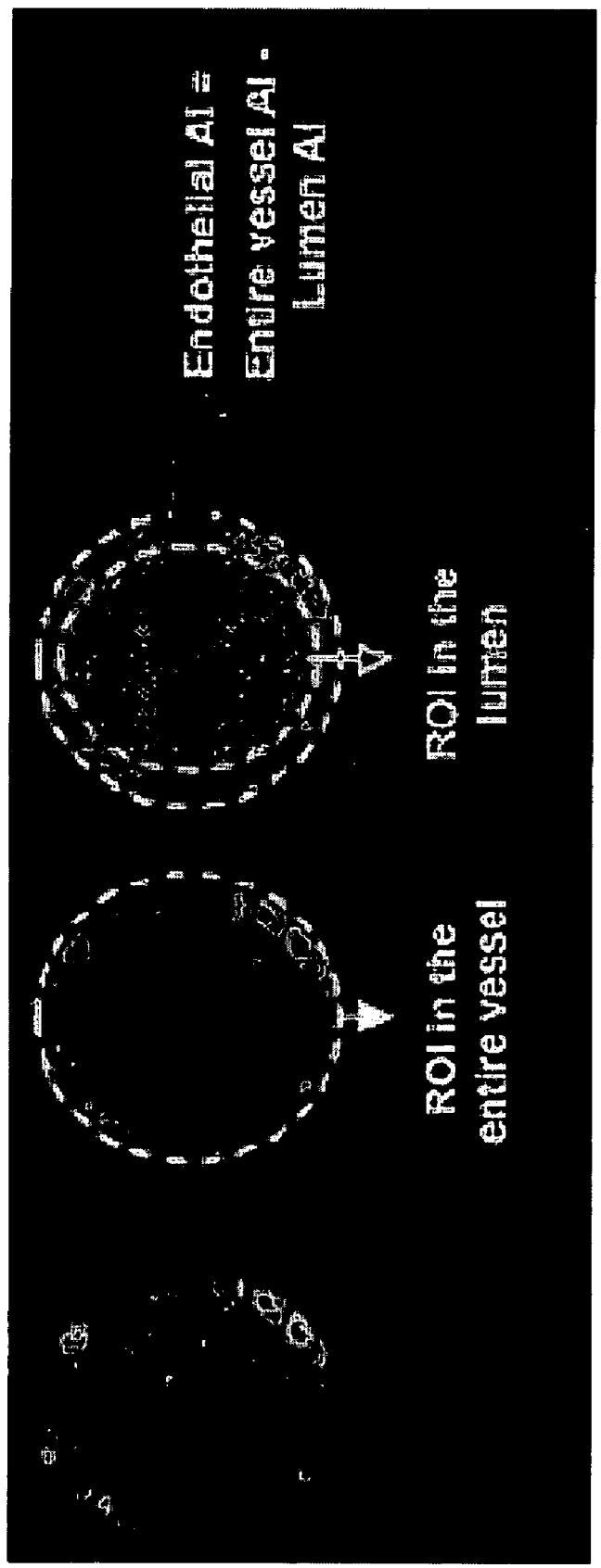
FIG. 2A is a transverse sectional image of a carotid artery obtained with a low mechanical index real-time pulse sequence after intravenous injection of albumin-encapsulated microbubbles. The cross-sectional region of the entire vessel (one region of interest) and of the lumen (the second region of interest) is indicated.
Figure 2B:
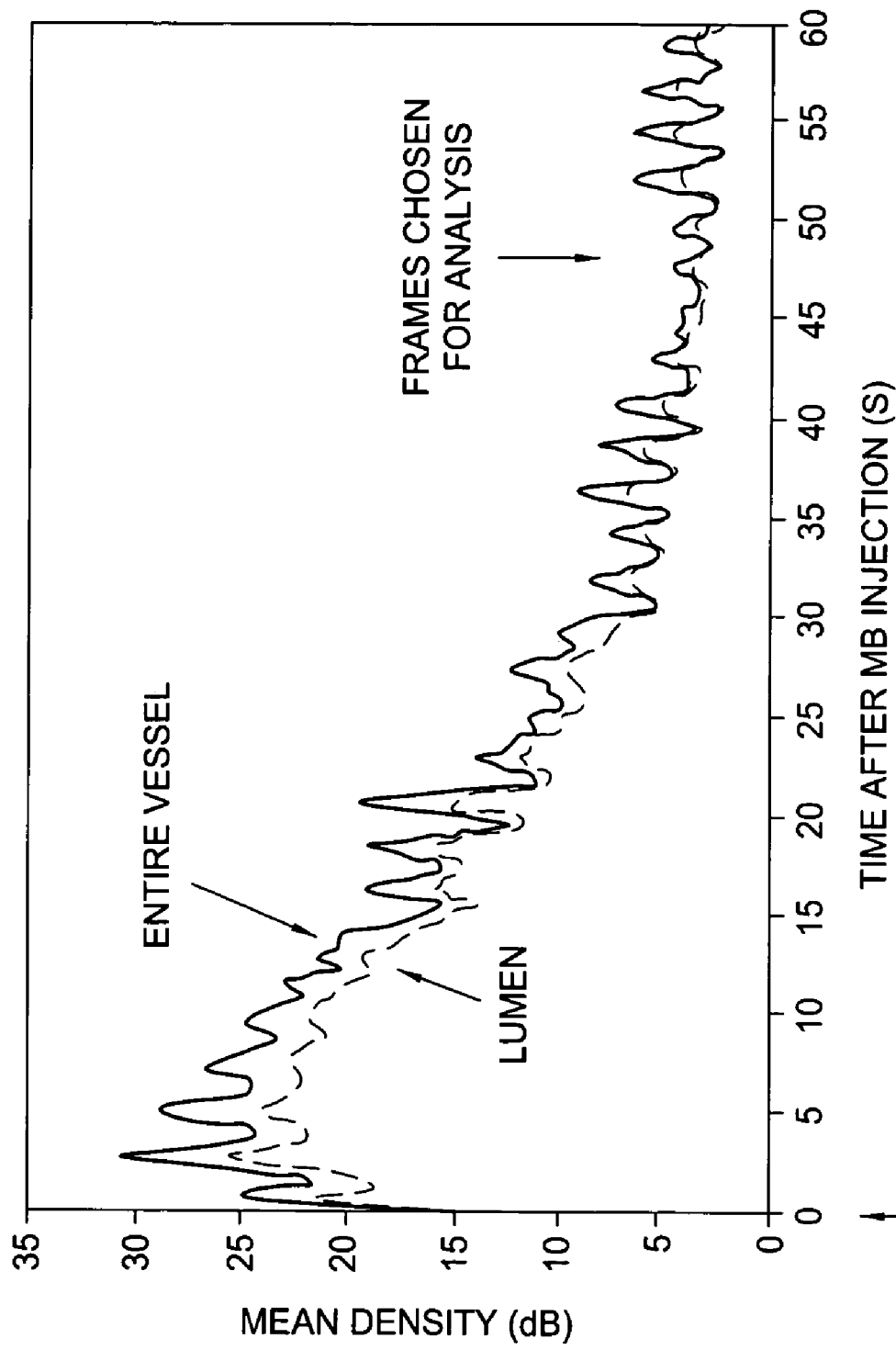
FIG. 2B is a graph of acoustic intensity (in dB) versus time. Quantification of the mean acoustic intensity was performed simultaneously in both regions of interest and the late 50 frames after clearance of free flowing microbubbles were chosen for analysis. Endothelial acoustic intensity was defined as the difference between the mean entire vessel acoustic intensity minus the lumen acoustic intensity.

Quantification of the contrast acoustic intensity was performed off-line using a specific program (CUSQ 1.3, Siemens Acuson, Mountain View, Calif.). Transverse sectional views of the carotid artery were used for analysis. Quantification of the entire vessel acoustic intensity (encompassing the endothelial border and central lumen) was obtained by placing a region of interest just inside the vessel border on the transverse carotid image. Quantification of lumen acoustic intensity was obtained by placing a smaller region of interest in the central part of the lumen excluding the endothelial border, as shown in FIG. 2A. The mean acoustic intensity of both regions was measured simultaneously. For each sequence of images at baseline, post-intralipid infusion and post-carotid artery balloon dilatation, 50 consecutive frames were analyzed in the late period of PESDA injection after clearance of free-flowing microbubbles (FIG. 2B). A typical bolus injection resulted in a 20–25 second period of complete vessel opacification, followed by a washout period. Therefore, the sequence of frames chosen for quantification of acoustic intensity was initiated at a mean of 30 seconds after the first detection of microbubbles in the carotid artery. Endothelial acoustic intensity was defined as the difference between the entire vessel acoustic intensity minus the lumen acoustic intensity, and expressed as the mean of 50 sequential frames.

Pathological Analysis of Carotid Artery

Following the final evaluation of the carotid artery responses to acetylcholine infusion, the pigs were sacrificed and sections of both the balloon-dilated and the contralateral carotid artery (controls) were excised and fixed in 10% formalin solution for a minimum of 48 hours. In two pigs, a final PESDA microbubble injection was performed without any ultrasound in order to detect the presence of adherent microbubbles by scanning electron microscopy.

For scanning electron microscopy, the carotid arteries were longitudinally sectioned and dehydrated through series of ethanol concentrations increasing from 5% to 100%. The specimens were then immersed in Freon 113, critical point dried, mounted in aluminum stubs and sputter-coated with gold (Polaron E5100, Polaron, Inc.). Analyses were performed using a Philips 515 scanning electron microscope (Philips Inc., Eindhoven, The Netherlands).

Statistical Analysis

Continuous data are expressed as mean±standard deviation. Comparisons of endothelial acoustic intensity before and after procedures and differences in vessel responses to acetylcholine infusion were performed by a paired t test and/or Wilcoxon test, as appropriate. An unpaired Student's t test was used for comparison of endothelial acoustic intensity in the balloon-injured and control vessels. Hemodynamic parameters were compared by analysis of variance. A p value of <0.05 was considered statistically significant.

Baseline Measurements

A clear visualization of microbubble transit in real-time was obtained by imaging the carotid artery with a high frequency transducer equipped with a contrast pulse sequence at a mechanical index of 0.3. No bubbles were visualized late (>30 seconds) after PESDA injections except in the one pig. Carotid artery response to acetylcholine was vasodilatation in 4 of the 5 pigs at baseline (FIG. 4A), and a vasoconstrictive response was observed in the pig that exhibited endothelial retention of microbubbles at baseline.

Intralipid Infusion and Carotid Artery Stretching Results

Serum triglyceride levels were within the normal range in all pigs at baseline, showed a significant increase after intralipid infusion, and returned to near baseline levels at 2 hours post infusion (see Table 1).

TABLE 1

Lipid levels at baseline and post intralipid infusion.

|  | Baseline | Post intralipid | Two hours later |
|---|---|---|---|
| Triglyceride (mg/dl) | 13 ± 7 | 442 ± 334 | 27 ± 28# |
| Total Cholesterol (mg/dl) | 72 ± 11 | 82 ± 17 | 77 ± 8† |

Values are mean ± SD. * $p < 0.05$ between groups by ANOVA; #p = NS between baseline and two hours later; †p = NS between groups by ANOVA.

After intralipid infusion, retention of microbubbles in the endothelium was observed in all pigs and was imaged as a ring around the vessel in both the right and left carotid arteries.

Figure 3A:
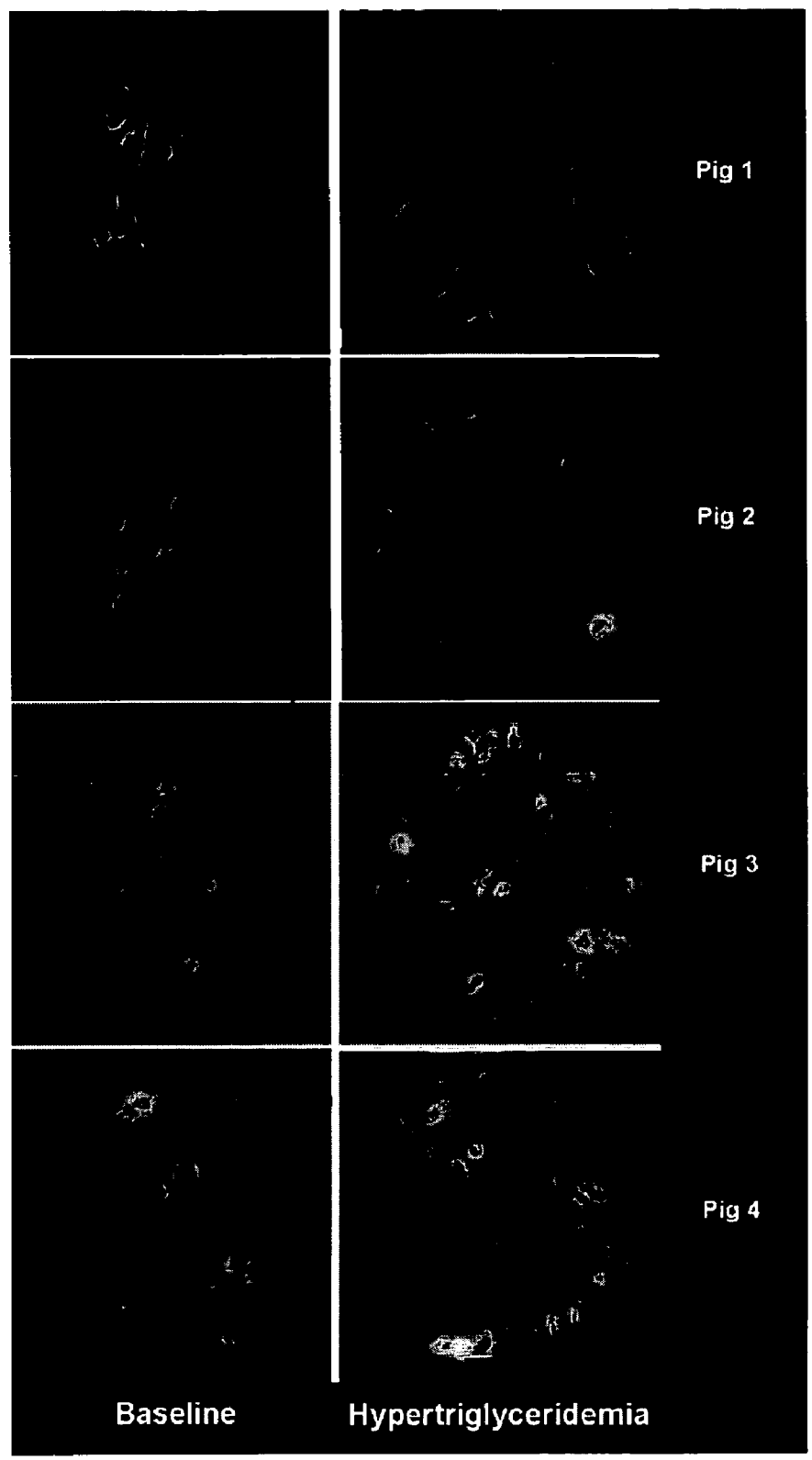
FIG. 3A shows transverse sectional images of carotid arteries of four pigs obtained with low mechanical index real-time pulse sequence scheme after intravenous injection of albumin-encapsulated microbubbles. The panels on the left show images of untreated arteries and the panels on the right show images after intralipid infusion.
Figure 3C:
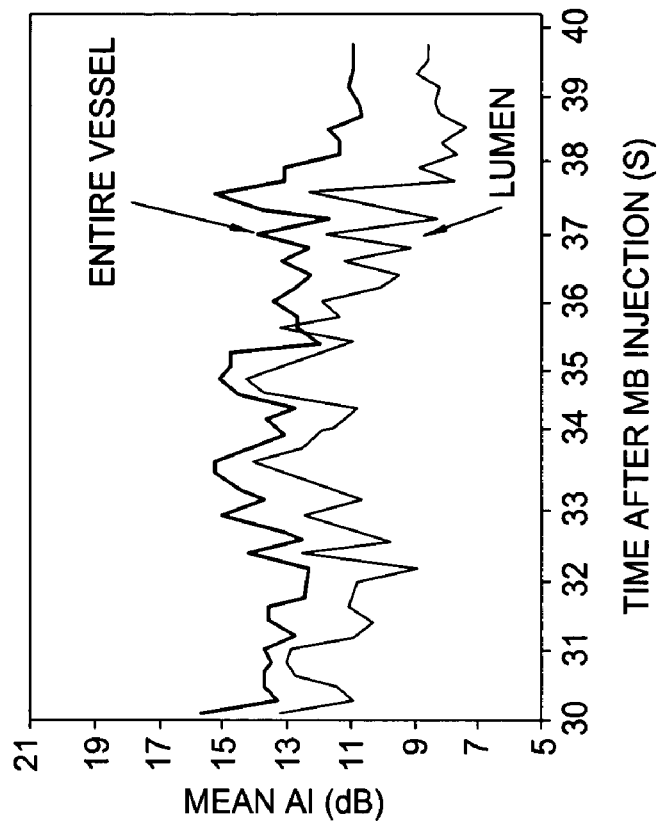
FIG. 3B shows time/acoustic intensity data for the untreated arteries and FIG. 3C shows time/acoustic intensity data for the lipid-infused arteries.
Figure 3B:
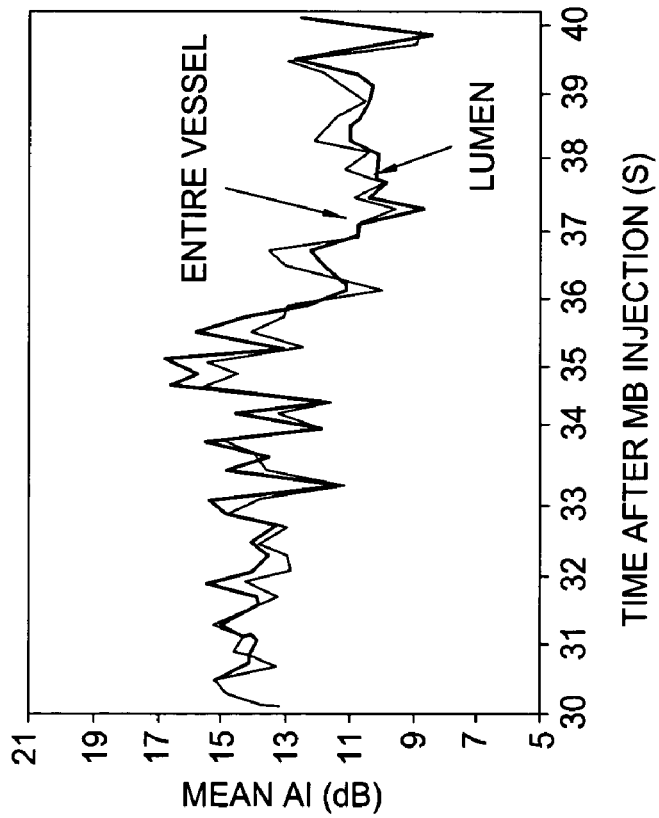

FIG. 3A shows transverse sectional images of carotid arteries of four pigs obtained with low mechanical index real-time pulse sequence scheme after intravenous injection of albumin-encapsulated microbubbles. The panels on the left show images of untreated arteries and the panels on the right show images after intralipid infusion. Note the presence of retained microbubbles in a clearing around the vessel lumen of the arterial wall after the intravenous injection of microbubbles. Microbubbles retained in a ring were observed only during hypertriglyceridemia. FIG. 3B shows time/acoustic intensity data for the untreated arteries and FIG. 3C shows time/acoustic intensity data for the lipid-infused arteries. The entire vessel (top line) mean acoustic intensity was higher than the lumen (bottom line) acoustic intensity, due to the increased intensity of retained microbubbles in the endothelium, not observed at baseline. The mean endothelial acoustic intensity increased by 1.0±1.3 dB during hypertriglyceridemia ($p<0.001$). A significant increase in the endothelial acoustic intensity was detected in all carotid arteries, except in the right carotid of the pig in which microbubble adherence to carotid artery wall was detected even at baseline.

FIG. 4 shows carotid artery diameter response to intra-arterial infusion of acetylcholine at baseline during hypertriglyceridemia (A) and after arterial balloon dilatation (B). The carotid response went from dilation at baseline to constriction after intralipid infusion and balloon dilatation, confirming the presence of endothelial dysfunction in both conditions.

Figure 4B:
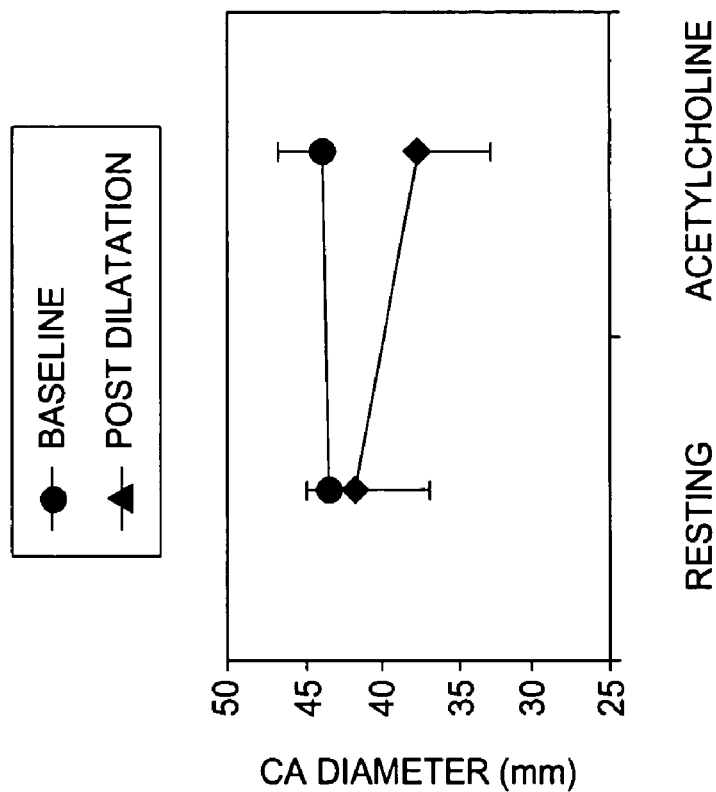
FIG. 4 shows carotid artery diameter response to intra-arterial infusion of acetylcholine at baseline during hypertriglyceridemia (A) (p=0.024), and after arterial balloon dilatation (B) (p=0.02).
Figure 4A:
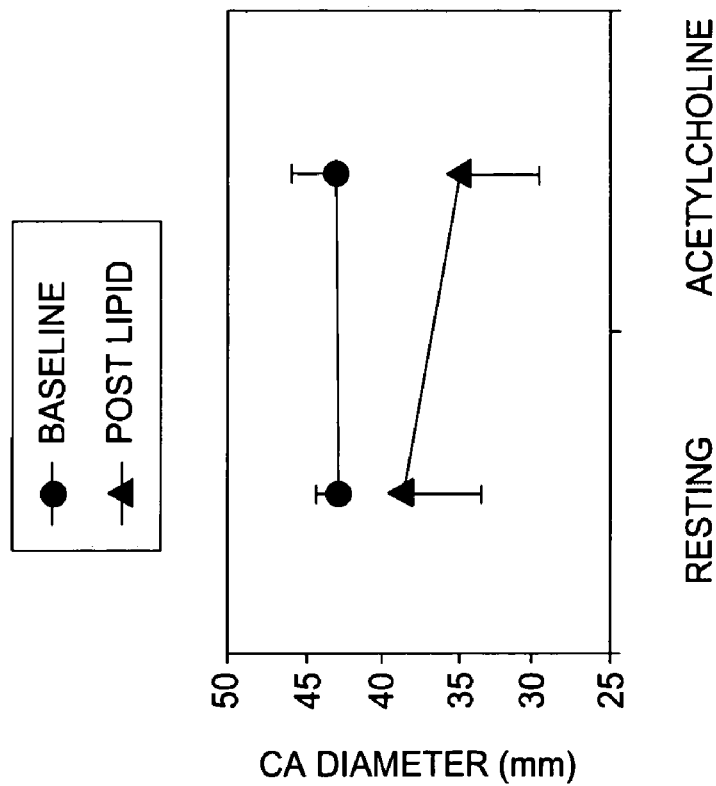

The presence of endothelial dysfunction during hypertriglyceridemia was confirmed by carotid artery response to acetylcholine. As stated previously, one pig exhibited an abnormal retention of microbubbles to carotid artery as well as a vasoconstrictive response to acetylcholine at baseline. When this pig was excluded from the global analysis, the carotid artery response to acetylcholine went from vasodilatation at baseline to vasoconstriction during hypertriglyceridemia ($p=0.024$) (FIG. 4A).

Carotid artery dilatation by balloon angioplasty was successfully performed in 6 vessels. In one pig there was dissection and occlusion of the left carotid artery during the procedure. Dilatation of the right carotid was subsequently performed and used for analysis. The remaining 5 contralateral carotid arteries served as controls. The endothelial acoustic intensity in the stretched carotid arteries measured after the procedure (0.68±1.28 dB) was significantly higher than the endothelial acoustic intensity in the control carotid arteries (−0.39±1.22 dB; $p<0.01$). Endothelial dysfunction in the stretched vessels was confirmed by a vasoconstrictive response to intra-arterial infusion of acetyloholine, as shown in FIG. 4B.

There were no significant differences in the arterial blood pressures or heart rates between baseline, post intralipid and post dilatation conditions (Table 2).

TABLE 2

Hemodynamic data.

|  | Baseline | Post intralipid | Post dilatation |
|---|---|---|---|
| HR (bpm) | 113 ± 14 | 104 ± 17 | 105 ± 9† |
| SBP (mm Hg) | 86 ± 8 | 96 ± 12 | 86 ± 15† |
| DBP (mm Hg) | 53 ± 9 | 67 ± 15 | 56 ± 17† |

Values are mean ± SD. DBP = diastolic blood pressure; HR heart rate; SBP = systolic blood pressure. †p = NS between groups by ANOVA.

Scanning Electron Microscopy

Figure 5:
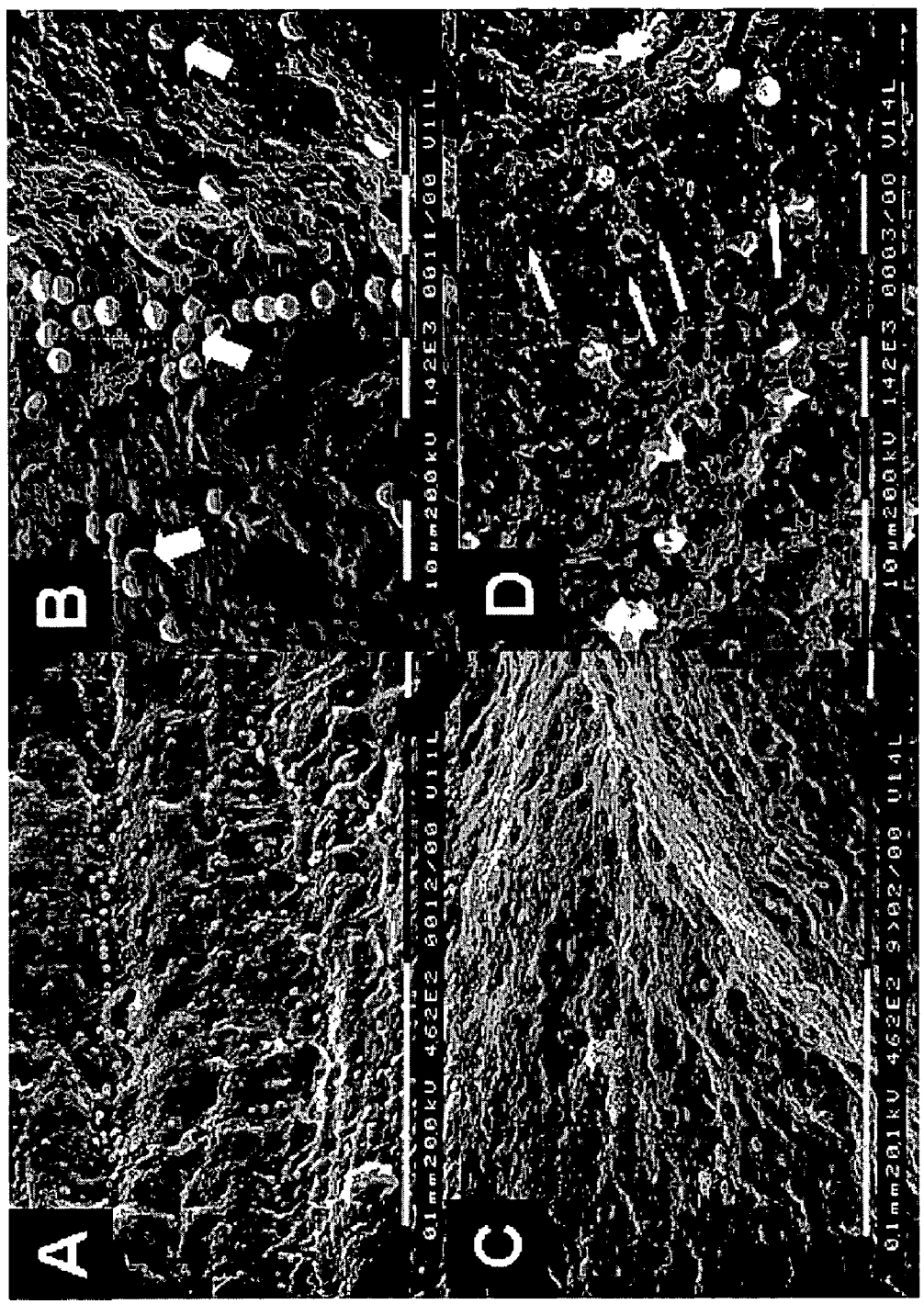
FIG. 5 shows four scanning electron micrographs of balloon-dilated carotid arteries seen at low magnification (0.1 mm) (462×) on the left and high magnification (10 μm) (1420×) on the right. Panels A and B show the images of a dilated vessel in which PESDA microbubbles were injected just before animal sacrifice, with no further insonification. Panels C and D represent the scanning electron micrograph images of a stretched artery in which high mechanical index ultrasound scanning was performed.

Scanning electron microscopy demonstrated evidence of endothelial stretching with minimal denudation in all balloon-dilated vessels. FIG. 5 shows four scanning electron micrographs of balloon-dilated carotid arteries seen at low magnification (0.1 mm) (462×) on the left and high magnification (10 μm) (1420×) on the right. Panels A and B show the images of a dilated vessel in which PESDA microbubbles were injected just before animal sacrifice, with no further insonification. Note the presence of numerous microbubbles attached to the injured endothelium (A) (462×). With higher magnification (B) (1420×) the microbubbles can be differentiated clearly them from the disc shaped red blood cells (large white arrows). Panels C and D represent the scanning electron micrograph images of a stretched artery in which high mechanical index ultrasound scanning was performed. There are few microbubbles attached to the injured endothelium (black arrow) and many holes in the endothelial membrane (small white arrows).

Endothelium in the control vessel appeared normal. Denudation of the endothelial layer was observed only in restricted areas of the injured carotid artery, with disruption of the endothelial cell membranes and separation of the cell junctions. In one pig there was evidence of stretching of the endothelial layer, with no denudation.

Scanning electron microscopy also revealed presence of microbubbles retained in both the denuded areas and to the endothelial cells adjacent to the regions where denudation occurred. Microbubbles were characterized as less electron-dense structures, with a size of 3 to 5 microns, spherically-shaped (differentiating them from disc shaped red blood cells) and devoid of surface characteristics of endothelial cells, like microvilli or microridges. The microbubbles adherent to the endothelium were observed in highest number in the stretched carotid artery of the pigs in which a final PESDA injection was given without ultrasound prior to sacrifice (FIG. 5). In the pigs that were insonified by high mechanical index imaging for evaluation of the carotid response to acetylcholine, there was a lower number of microbubbles and some holes or pockets in the endothelium were detected, most likely representing areas of microbubble destruction by ultrasound (FIGS. 5 and 6).

Figure 6:
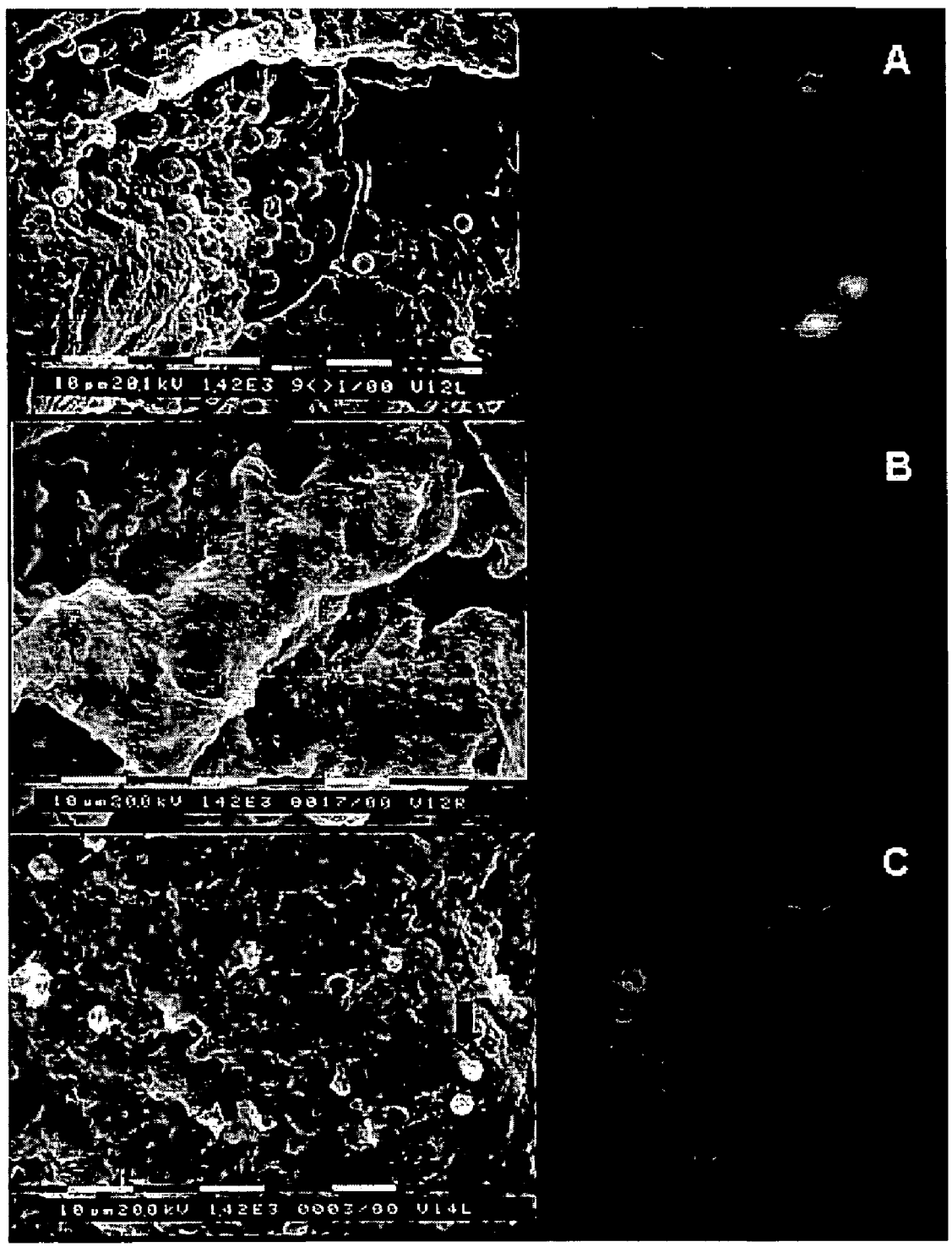
FIG. 6 shows high-magnification scanning electron micrograph (left panels) (1420×) and the corresponding low mechanical index pulse sequence scheme images (right panels). Figure A demonstrates the presence of microbubbles retained in the endothelium detected by a pulse sequence scheme in a stretched left carotid artery and Figure B demonstrates the absence of microbubbles in the endothelium in the control right carotid artery. Panel C shows the pulse sequence scheme image of a stretched vessel of a second pig in which the scanning electron micrograph was performed after insonification of the carotid artery with high mechanical index imaging.

FIG. 6 shows high-magnification scanning electron micrograph (left panels) and the corresponding low mechanical index pulse sequence scheme images (right panels). Figure A demonstrates the presence of microbubbles retained in the endothelium detected by a pulse sequence scheme in a stretched left carotid artery and Figure B demonstrates the absence of microbubbles in the endothelium in the control right carotid artery. In this pig, microbubbles were injected just prior to sacrifice without further insonification, and the scanning electron micrograph revealed sites of injury with endothelial denudation and attachment of microbubbles (black arrows) to the denuded endothelium only in the injured vessel (A) and normal appearing endothelium in the control vessel (B). Panel C shows the pulse sequence scheme image of a stretched vessel of a second pig in which the scanning electron micrograph was performed after insonification of the carotid artery with high mechanical index imaging. Note the presence of few microbubbles (black arrows) attached to the injured endothelium, and holes that most likely represent areas of microbubbles destruction by the ultrasound.

While the present invention has been described with reference to specific embodiments, it should be understood by those skilled in the art that various changes may be made and equivalents may be substituted without departing from the true spirit and scope of the invention. In addition, many modifications may be made to adapt a particular situation, material, or process to the objective, spirit and scope of the present invention. All such modifications are intended to be within the scope of the invention.

The invention claimed is:

1. A method for identifying early dysfunctional vascular endothelium in a vessel of interest in an individual, comprising:
    injecting the individual with microbubbles; and
    performing transcutaneous imaging of the vessel of interest using a low mechanical index pulse sequence which is adapted to identify direct adherence of the microbubbles to the dysfunctional vascular endothelium wherein the adherence of microbubbles in the vessel identifies dysfunctional vascular endothelium.

2. The method of claim 1, wherein the low mechanical index is about 0.03 to about 0.4.

3. The method of claim 2, wherein the low mechanical index is about 0.05 to about 0.3.

4. The method of claim 1, wherein the vessel of interest is an artery.

5. The method of claim 4, wherein the artery is a carotid artery.

6. The method of claim 1, wherein the microbubbles comprise one or more proteins, polymer materials, carbohydrates, lipids, phospholipids or surfactants.

7. The method of claim 6, wherein the protein is albumin, apotransferrin, urease, alpha-1-antitrypsin, alpha fetoprotein, aminotransferases, amylase, C-reactive protein, carcinoembryonic antigen, ceruloplasmin, complement, creatine phosphokinase, ferritin, fibrinogen, fibrin, transpeptidase, gastrin, serum globulins, hemoglobin, myoglobin, immunoglobulins, lactate dehydrogenase, lipase, lipoproteins, acid phosphatase, alkaline phosphatase, alpha-1-serum protein fraction, alpha-2 serum protein fraction, beta protein fraction, gamma protein fraction, gamma-glutamyl transferase, or gelatin.

8. The method of claim 7, wherein the protein is albumin.

9. The method of claim 6, wherein the polymer is a biodegradable polymer.

10. The method of claim 6, wherein the carbohydrate is a hexose; disaccharide; pentose; alpha-, beta-, or gamma-cyclodextrin; polysaccharide or sugar alcohol.

11. The method of claim 6, wherein the phospholipids is lecithin, a lecithin derivative, a phosphatidic acid; a phosphatidylethanolamine; a phosphatidylserine; a phosphatidylglycerol; a phosphatidylinositol; cardiolipin; or a sphingomyelin.

12. The method of claim 6, wherein the surfactant is a fatty acid, a fluorine-containing phospholipid, a polyethylene glycol, a block copolymer surfactant, phosphatidylserine, phosphatidylglycerol, phosphatidylinositol, phosphatidic acid or cardiolipin.

13. The method of claim 1, wherein the microbubbles comprise a gas.

14. The method of claim 13, wherein the gas is air, nitrogen, oxygen, carbon dioxide, hydrogen, helium, argon, neon, xenon or krypton, or a halogenated hydrocarbon.

15. The method of claim 14, wherein the halogenated hydrocarbon is perfluoromethane, perfluoroethane, perfluoropropane, perfluorobutane, perfluoropentane, perfluorohexane, perfluoroheptane; perfluoropropene, perfluorobutenes, perfluorobutadiene, perfluoropentene, perfluorocyclobutane, perfluoromethylcyclobutane, perfluorodimethylcyclobutane, perfluorotrimethylcyclobutane, perfluorocyclopentane, perfluoromethylcyclopentane, perfluorodimethylcyclopentans, perfluorocyclohexane, perfluoromethylcyclohexane or perfluorocycloheptane.

16. The method of claim 1, wherein the microbubbles consist essentially of albumin, an aqueous sugar solution and a perfluorocarbon gas.

17. The method of claim 16, wherein the sugar is glucose, galactose, fructose, sucrose, lactose, maltose, amylase, dextran or mixtures thereof.

18. The method of claim 17, wherein the sugar is dextrose.

19. The method of claim 16, wherein the perfluorocarbon gas is perfluoromethane, perfluoroethane, perfluoropropane, perfluorobutane or decafluorobutane or mixtures thereof.

20. The method of claim 16, wherein the microbubbles comprise one to five parts albumin to one to five parts dextrose.

21. The method of claim 16, wherein the albumin, sugar and perfluorocarbon gas are sonicated to form the microbubbles.

22. The method of claim 1, wherein the microbubbles are about 2.0 to about 8.0 microns in diameter.

23. The method of claim 22, wherein the microbubbles are about 4.0 to about 6.0 microns in diameter.

24. The method of claim 1, wherein a frequency of the low mechanical index pulse sequence is about 1.5 to about 15.

25. The method of claim 1, wherein the low mechanical index pulse sequence is performed with a frame rate of about 20 to 30 Hz.

26. A method for imaging identifying early dysfunctional vascular endothelium in an artery in an individual, comprising:
    injecting the individual with microbubbles consisting essentially of albumin, an aqueous sugar solution and a perfluorocarbon gas; and
    performing transcutaneous imaging of the vessel of interest using a pulse sequence with a mechanical index of about 0.03 to about 0.4 which is adapted to identify direct adherence of the microbubbles to the dysfunctional vascular endothelium, wherein the adherence of microbubbles in the vessel identifies dysfunctional vascular endothelium.

27. The method of claim 26, wherein the low mechanical index is about 0.05 to about 0.3.

28. The method of claim 26, wherein the vessel of interest is an artery.

29. The method of claim 26, wherein the sugar is glucose, galactose, fructose, sucrose, lactose, maltose, amylase, dextran or mixtures thereof.

30. The method of claim 29, wherein the sugar is dextrose.

31. The method of claim 26, wherein the perfluorocarbon gas is perfluoromethane, perfluoroethane, perfluoropropane, perfluorobutane or decafluorobutane or mixtures thereof.

32. The method of claim 26, wherein the microbubbles comprise one to five parts albumin to one to five parts dextrose.

33. The method of claim 26, wherein the albumin, sugar and perfluorocarbon gas are sonicated to form the microbubbles.

34. The method of claim 26, wherein the microbubbles are about 2.0 to about 8.0 microns in diameter.

35. The method of claim 34, wherein the microbubbles are about 4.0 to about 6.0 microns in diameter.

36. The method of claim 26, wherein a frequency of the low mechanical index pulse sequence is about 1.5 to about 15.

37. The method of claim 26, wherein the low mechanical index pulse sequence is performed with a frame rate of about 20 to 30 Hz.

* * * * *

UNITED STATES PATENT AND TRADEMARK OFFICE
CERTIFICATE OF CORRECTION

PATENT NO.         : 7,025,726 B2                                            Page 1 of 1
APPLICATION NO. : 10/764294
DATED              : April 11, 2006
INVENTOR(S)      : Thomas R. Porter and Feng Xie It is certified that error appears in the above-identified patent and that said Letters Patent is hereby corrected as shown below:

Column 5, Line 13: Change "amincoethyldextran" to --aminoethyldextran--

Column 8, Line 37: Change "that" to --than--

Column 11, Line 19: Change "cariotid" to --carotid--

Column 13, Line 66: Change "acetyloholine" to --acetylcholine--

In the Claims

Column 16, Claim 15, Line 17: Change "perfluorodimethylcyclopentans" to --perfluorodimethylcyclopentane--

Column 16, Claim 26, Line 44: Delete "imaging"

Signed and Sealed this

Fifth Day of September, 2006

JON W. DUDAS
*Director of the United States Patent and Trademark Office*